(12) United States Patent
Hiles

(10) Patent No.: US 9,492,267 B2
(45) Date of Patent: Nov. 15, 2016

(54) CELL-SEEDED EXTRACELLULAR MATRIX GRAFTS

(75) Inventor: Michael C. Hiles, Lafayette, IN (US)

(73) Assignee: Cook Biotech Incorporated, West Lafayette, IN (US)

(*) Notice: Subject to any disclaimer, the term of this patent is extended or adjusted under 35 U.S.C. 154(b) by 1817 days.

(21) Appl. No.: 10/513,249

(22) PCT Filed: May 1, 2003

(86) PCT No.: PCT/US03/13467
§ 371 (c)(1),
(2), (4) Date: May 16, 2005

(87) PCT Pub. No.: WO03/092471
PCT Pub. Date: Nov. 13, 2003

(65) Prior Publication Data
US 2005/0202058 A1   Sep. 15, 2005

Related U.S. Application Data

(60) Provisional application No. 60/377,110, filed on May 2, 2002.

(51) Int. Cl.
| A61F 2/06 | (2013.01) |
| A61L 27/36 | (2006.01) |
| A61L 27/38 | (2006.01) |
| A61L 27/50 | (2006.01) |
| C12N 5/071 | (2010.01) |
| A61K 35/12 | (2015.01) |

(52) U.S. Cl.
CPC .............. *A61F 2/06* (2013.01); *A61L 27/3604* (2013.01); *A61L 27/3633* (2013.01); *A61L 27/383* (2013.01); *A61L 27/3804* (2013.01); *A61L 27/3808* (2013.01); *A61L 27/3826* (2013.01); *A61L 27/3886* (2013.01); *A61L 27/507* (2013.01); *C12N 5/0691* (2013.01); *A61K 35/12* (2013.01); *C12N 2533/92* (2013.01)

(58) Field of Classification Search
None
See application file for complete search history.

(56) References Cited

U.S. PATENT DOCUMENTS

| 4,902,508 | A |   | 2/1990  | Badylak et al. |           |
|-----------|---|---|---------|----------------|-----------|
| 4,956,178 | A |   | 9/1990  | Badylak et al. |           |
| 5,281,422 | A |   | 1/1994  | Badylak et al. |           |
| 5,352,463 | A | * | 10/1994 | Badylak et al. | ..... 424/551 |
| 5,554,389 | A |   | 9/1996  | Badylak et al. |           |
| 5,863,531 | A | * | 1/1999  | Naughton et al. | ..... 424/93.7 |
| 5,885,619 | A | * | 3/1999  | Patel et al.   | ..... 424/551 |
| 5,955,110 | A |   | 9/1999  | Patel et al.   |           |
| 6,099,567 | A |   | 8/2000  | Badylak et al. |           |
| 6,171,344 | B1| * | 1/2001  | Atala          | ..... 623/23.64 |
| 6,187,039 | B1|   | 2/2001  | Hiles et al.   |           |
| 6,206,931 | B1|   | 3/2001  | Cook et al.    |           |
| 6,358,284 | B1| * | 3/2002  | Fearnot et al. | ..... 623/23.72 |
| 6,475,232 | B1|   | 11/2002 | Babbs et al.   |           |
| 2003/0113302 | A1 |   | 6/2003 | Revazova et al. |          |

FOREIGN PATENT DOCUMENTS

| WO | WO 99/62424 | * 12/1999 |
| WO | WO 00/15765 |   3/2000 |
| WO | WO 01/10355 |   2/2001 |
| WO | WO 01/78754 |  10/2001 |
| WO | WO 02/07646 |   1/2002 |
| WO | WO 02/14460 |   2/2002 |

OTHER PUBLICATIONS

Weinberg et al, Science 1986, vol. 231, pp. 397-400.*
Sandusky et al, J Surg Res, Apr. 1995, vol. 58, No. 5, pp. 415-420.*
Block, S. "Peroxygen Compounds", Disinfection, Sterilization and Preservation, 4th Edition 1991, pp. 167-181. Philadelphia, Lea & Febiger.
Denton, G.W., "Chlorhexidine", Disinfection, Sterilization and Preservation, S.Block, editor, 4th Edition 1991, pp. 274-289. Philadelphia, Lea & Febiger.

* cited by examiner

*Primary Examiner* — Allison Fox
(74) *Attorney, Agent, or Firm* — Woodard, Emhardt, Moriarty, McNett & Henry LLP

(57) ABSTRACT

Described are tissue graft constructs that include an extracellular matrix material in combination with added endothelial cells and at least one additional added exogenous cellular population. The additional exogenous cellular population desirably includes muscle cells, such as smooth muscle cells, fibroblasts, or a combination thereof. Tubular constructs seeded with such cell combinations can be beneficially used as vascular grafts. Also described are methods for preparing and using such grafts.

19 Claims, 1 Drawing Sheet

CELL-SEEDED EXTRACELLULAR MATRIX GRAFTS

The instant application is a national stage entry under 35 USC 371 of PCT/US03/13467, filed May 1, 2003, which claims benefit of U.S. Provisional application 60/377,110, filed May 2, 2002.

BACKGROUND

The present invention is related generally to tissue grafts. More particularly, the present invention is related to tissue graft prosthesis devices including an extracellular matrix material, endothelial cells, and at least one additional exogenous population of cells.

SUMMARY OF THE INVENTION

In one embodiment, the present invention provides a tissue graft prosthesis comprising an extracellular matrix material, preferably submucosa, added endothelial cells, and at least one additional added exogenous cell population. In preferred forms, the tissue graft prosthesis is in the form of a tube and is useful, for example, as a vascular graft. More preferably, the at least one additional exogenous population is a population of fibroblasts, a population of smooth muscle cells, or both.

The present invention also provides methods for grafting a patient comprising implanting in the patient a tissue graft construct as described above.

The present invention also provides methods for making tissue graft constructs. These methods comprise providing an extracellular matrix material; seeding endothelial cells in vitro on the material; and, seeding at least one additional exogenous population of cells on the material in vitro.

In another embodiment, the present invention provides a tubular graft prosthesis, such as a vascular graft prosthesis, comprising a biodegradable or non-biodegradable support, a tubular construct comprising a collagenous extracellular matrix material attached to the support, and at least one cell type, preferably including endothelial cells, smooth muscle cells, fibroblast cells, or any combination thereof, seeded upon the extracellular matrix material.

DESCRIPTION OF THE PREFERRED EMBODIMENTS

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As disclosed above, the present invention provides certain cell-seeded tissue graft constructs and methods of their manufacture and use.

In accordance with the invention, the tissue graft construct includes an extracellular matrix material. Suitable such materials include, for example, submucosa, dura mater, pericardium, serosa, peritoneum or basement membrane tissues, including liver basement membrane. Suitable submucosa tissues for these purposes include, for instance, intestinal submucosa including small intestinal submucosa, stomach submucosa, urinary bladder submucosa, and uterine submucosa. These extracellular matrix materials may be derived generally from warm-blooded vertebrates, more preferably mammals such as porcine, bovine or ovine mammals. Human donor tissues may also be used. These extracellular matrix materials may be used in any suitable form, including their use as layers. In preferred embodiments, the extracellular matrix material is used in layer form, and is formed into a tube.

The endothelial cells for use in the invention, or precursors thereto, can be derived from any suitable source of endothelial cells including vascular endothelial cells from arterial or venous tissues.

The additional exogenous cell population may be any cell population adding to the functional characteristics or durability of the tissue graft construct. In preferred embodiments of the present invention, the additional exogenous cell population includes muscle cells or precursors to muscle cells. Smooth muscle cells or their precursors are preferred. Suitable muscle cells and precursor cells for use in the invention are disclosed, for example, in WO 178754 published Oct. 25, 2001.

In another preferred embodiment, the additional cells include fibroblasts, or precursors thereto. In still a further preferred embodiment, endothelial cells, preferably vascular endothelial cells, fibroblasts, and smooth muscle cells (or precursors to any of these cells) are all seeded onto the graft construct.

Tissue graft constructs of the invention preferably takes the form of a tubular construct. Cells may be seeded onto the interior (lumenal) surface, the exterior surface, or both.

Figure 1:
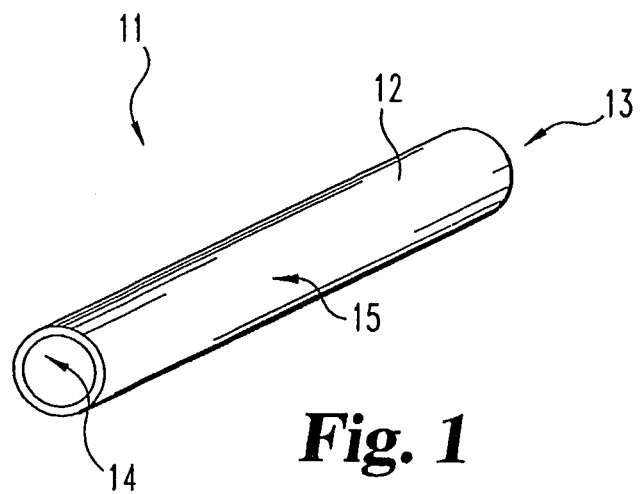
FIG. 1 provides a perspective view of a tubular graft construct of the invention.
Figure 2:
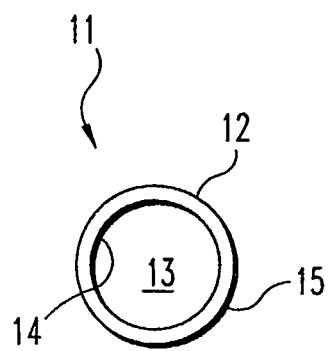
FIG. 2 provides a cross-sectional view of the construct of FIG. 1.

With specific reference now to FIGS. 1 and 2, provided is a tubular tissue graft construct 11 of the invention. Tubular tissue graft construct includes a generally cylindrical wall 12 defining an interior lumen 13. In accordance one preferred embodiment of the invention, the lumenal surface 14 of the construct 11 is populated with endothelial cells, preferably vascular endothelial cells. At least one additional exogenous cell population, preferably muscle cells such as smooth muscle cells, and/or fibroblasts, is also included on the construct. Such tissue grafts provide advanced functionality and durability beneficial to replacement vessels for use in patients, including human patients.

Various constructs can be made in accordance with the invention. For example, in a first illustrative embodiment, the lumenal surface 14 includes endothelial cells only. The exterior surface 15 includes muscle cells, fibroblast cells, or a combination thereof. In a second illustrative embodiment, the lumenal surface 14 includes endothelial cells and muscle cells. Preferably, in this arrangement, endothelial cells will be presented to the lumenal surface, either alone as a layer atop a layer of muscle cells, or in admixture with the muscle cells. In this second embodiment, the exterior surface 15 may include one or both of muscle cells and fibroblast cells, potentially in combination also with endothelial cells. In these embodiments, the endothelial cells are desirably vascular endothelial cells, and the muscle cells are desirably smooth muscle cells.

Cells utilized in graft constructs of the invention are preferably human cells. The cells may be autologous to a patient to be treated, allogenic to the patient to be treated, or xenogenic to the patient to be treated. The cells may be derived and potentially expanded from biopsy tissue, or may be derived from stable cell lines, including human cell lines.

Cells may be seeded onto the extracellular matrix material using any suitable methods. In this regard, the various cell types can be seeded onto the material together, or separately. This seeding process may occur at any time up to the implantation of the graft in the patient. The seeding process may involve the expansion of the cells prior to implantation, or may lack any such expansion. Moreover, one cell type may be expanded, whereas another may not. When expanding or otherwise culturing cells, suitable culture conditions may be used as known in the art.

In preferred embodiments, walls 12 of construct 11 (FIGS. 1 and 2), can be formed of one or more layers of extracellular matrix material, for example including one to about four or more layers of extracellular matrix material. These layers may be bonded to another by any suitable method. These include, for example, the use of biocompatible adhesives such as collagen pastes, fibrin glue, and the like. Layers may also be dehydrothermally bonded to one another, for example by compressing overlapped regions under dehydrating conditions.

The extracellular matrix material used in the invention may be purified and sterilized in any suitable manner. The preferred purification processes of the invention will involve contacting the material with an appropriate agent or agents. For example, and not by way of limitation, this may include tanning with glutaraldehyde and formaldehyde, treatment with oxidizing compounds, gas plasma sterilization, gamma radiation, and combinations thereof. In this regard, desirable processes of the invention involve exposing the isolated extracellular matrix material to a solution containing one or more oxidizing agents, preferably peroxy compounds, more preferably organic peroxy compounds, and most preferably peracids. When a peracid is used, it is desirably selected from the group consisting of peracetic acid, perpropionic acid and perbenzoic acid. Peracetic acid is most preferred. Other peroxy disinfecting agents, for example, hydrogen peroxide, are also suitable for use. Still other suitable peroxy compounds are described in "Peroxygen Compounds", S. Block, in Disinfection, Sterilization and Preservation, S. Block, Editor, 4th Edition, Philadelphia, Lea & Febiger, pp. 167-181, 1991; and "Disinfection with peroxygens" M. G. C. Baldry and J. A. L. Fraser, in Industrial Biocides, K. Payne, Editor, New York, John Wiley and Sons, pp. 91-116, 1988. While peroxy compounds are preferred, other oxidizing agents, for example, chlorine agents such as chlorhexidine (1,6-di(4-chlorophenyldiguanido)hexane) in its digluconate form may also be used. Many other suitable chlorine agents are described in "Chlorhexidine", G. W. Denton, in Disinfection, Sterilization and Preservation, S. Block, Editor, 4th Edition, Philadelphia, Lea & Febiger, pp. 274-289, 1991.

The preferred solvent for diluting the oxidizing agent is aqueous alcohol. Preferably the alcohol content is from about 1% to about 30% by volume of the solution, and more preferably the alcohol content is between about 2% to about 10% by volume. It is contemplated that many alcohols may be used to form the aqueous alcohol solution. However, it is preferred that the alcohol contains from 1 to about 6 carbon atoms; more preferred that the alcohol is selected from a group consisting of ethanol, propanol, isopropanol, denatured alcohol and butanol; and most preferred that the alcohol is either ethanol or denatured alcohol. In addition, the solution preferably has a pH of about 1.5 to about 10, more preferably a pH of about 2 to about 6, and most preferably a pH of about 2 to about 4. Although not necessary, conventional buffers may be used to adjust the pH, and the choice of buffers is within the knowledge of those skilled in the art.

The isolated extracellular matrix material will be exposed to the above-described processing agents for a suitable period of time. Generally, exposure can entail submersing the isolated material into a solution under agitation. The exposure time is typically at least about 5 minutes, for example in the range of about 15 minutes to about 40 hours, and more typically in the range of about 0.5 hours to about 8 hours. Also, preferably, the extracellular matrix material is pre-rinsed with a solvent, for example sterile water, before exposure to the processing solution.

One preferred purification procedure of the invention is exposing the extracellular matrix material to dilute peracetic acid. The peracetic acid is diluted with an aqueous alcohol solution containing about 2% to about 10% by volume alcohol. The concentration of the peracetic acid may range, for example, from about 0.05% by volume to about 1.0% by volume. Most preferably the concentration of the peracetic acid is from about 0.1% to about 0.3% by volume. When the peracetic acid content is about 0.2%, the matrix material can be exposed for about two hours. The exposure time can of course be longer or shorter, depending upon the particular agent used, its concentration, and other factors within the purview of those skilled in the art.

In preferred purification processes wherein the extracellular matrix material is submucosa, for example small intestinal submucosa, a source tissue can be disinfected prior to harvesting the submucosa. Suitable such procedures are disclosed, for example, in U.S. Pat. No. 6,206,931. In addition, preferred extracellular matrix materials, including submucosa materials, will desirably be processed so as to retain one or more bioactive components with which they occur. These may include, for example, one or more growth factors such as basic fibroblast growth factor (FGF-2), transforming growth factor beta (TGF-beta), epidermal growth factor (EGF), and/or platelet derived growth factor (PDGF). As well, extracellular matrix material used in the invention may include other biological materials such as heparin, heparin sulfate, hyaluronic acid, fibronectin and the like.

Further, preferred tissue processing techniques will be used to not only remove cell and cell debris, but also possible endogenous viruses, prion agents, and any contaminants introduced during harvesting of the extracellular matrix material. Illustratively, prion inactivation can be undertaken using sodium hydroxide treatment. Suitably, the material can be contacted with a solution of sodium hydroxide for a period of time sufficient to inactivate any prions present. The duration of contact will of course vary with the concentration of the sodium hydroxide solution, and potentially other factors known to those practiced in the relevant art. Illustratively, the tissue material may be contacted with a 0.1 N sodium hydroxide solution for 5 minutes to 5 hours, more preferably for 10 minutes to 2 hours, and most preferably for 15 to 60 minutes. Alternatively, more concentrated solutions of sodium hydroxide may be used, e.g. by contacting the tissue with 1.0 N sodium hydroxide for about 15-60 minutes. Still other prion inactivation treatments are known and can be used, including for example the use of steam sterilization under pressure, contact with a sodium hypochlorite solution (e.g. 2.5%), and the like.

The extracellular matrix material may be configured to a tubular form either before or after the cells are seeded onto the extracellular matrix material. For example, in certain embodiments, the cells are provided on the matrix material while the same is in a sheet configuration, and the sheet is thereafter configured to a tube, e.g. after a period of culturing in vitro. In other embodiments of the invention, extracellular matrix material is configured to a tube, and then cells are provided and potentially cultured for a period in vitro on the same. Further, some cells may be added while the extracellular matrix material is in sheet form, and others after configuration to a tube. For instance, cells to populate in the interior lumen of the construct may be added and potentially cultured with the extracellular matrix material in sheet form, the sheet form then being configured to a tube form, and additional cells then being added to the interior and/or exterior surfaces of the tube construct.

When adding and culturing cells with the extracellular matrix material in tube form, it may be preferable in some instances to provide a tubular support or other means to retain the material in its tube form as the cells are cultured, and to prevent any undesired bridging of cells across the interior lumen that may cause a deleterious blockage. The tubular support may, for example, be a wire stent or other biodegradable or non-biodegradable generally cylindrical support structure suitably designed and applied to the extracellular matrix material while permitting the desired attachment and culture of cells. Such tubular support may be designed for removal from the construct prior to implantation, or may be designed to be retained in the construct upon implantation. Other methods for retaining a tubular form during culture may include providing an internal pressure in the tube during culture, for example by flowing culture medium through the tube, or seeding cells within the tube along with sufficient culture medium to expand the tube to its desired form, and sealing the tube in this condition. In these and in other culturing processes, suitable measures will be taken to ensure the transfer of oxygen and nutrients to the cells as necessary for survival and potentially growth of the cells. Thus, seeded constructs may be cultured in tumbling or other agitated or perfused environments known to those skilled in the art.

To prepare tubular graft constructs of the invention, flat sheet extracellular matrix materials can be configured to a tubular form in any suitable manner. These include, for example, techniques in which a flat sheet of extracellular matrix material is configured into a tube shape, and sutured or otherwise bonded to retain the tube shape. Suitable methods for forming tubes of collagen tissues are disclosed in U.S. Pat. Nos. 6,187,039, 6,206,931 and 6,358,284, and in WO 0110355 published Feb. 15, 2001. It will be understood, however, the tissue graft constructs in sheet form or other non-tubular forms are also contemplated as a part of the present invention. For example, sheet- or patch-form constructs can be used as vascular patches, or in the repair of other damaged or diseased tissues.

For the purpose of promoting and additional understanding of the invention, the following specific examples are provided. It will be understood that these examples are illustrative, and not limiting, of the present invention.

EXAMPLE 1

Preparation of Cell-seeded Graft Construct

Small intestinal submucosa is harvested and prepared as described in U.S. Pat. No. 6,206,931. This small intestinal submucosa is formed into a single- or multi-layer tube using the techniques described in any one of U.S. Pat. Nos. 6,187,039, 6,206,931 and 6,358,284, and in WO 0110355 published Feb. 15, 2001. Vascular endothelial cells are added to the lumenal surface of the tube, and smooth muscle cells are added to the exterior surface of the tube. The tube can be immediately implanted or can be subjected to culture conditions suitable for the survival and growth of the cells.

EXAMPLE 2

Preparation of Cell-seeded Graft Construct

The procedure of Example 1 is repeated, except both vascular endothelial and smooth muscle cells are added to the lumenal surface of the construct. The construct can be immediately implanted or can be subjected to culture conditions suitable for survival and growth of the cells.

EXAMPLE 3

Preparation of Cell-seeded Graft Construct

The procedure of Example 1 is repeated, except both vascular endothelial and smooth muscle cells are added to the lumenal surface of the construct, and smooth muscle cells and fibroblast cells are added to the exterior surface of the construct. The construct can be immediately implanted or can be subjected to culture conditions suitable for survival and growth of the cells.

EXAMPLES 4-6

Preparation of Cell-seeded Graft Constructs

The procedures of examples 1-3 are repeated, except the submucosa tissue is in sheet form during the cell seeding and any culture period. Thereafter, the sheet is configured to a tubular form, and sutured longitudinally to create a substantially fluid-tight tube.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are indicative of the level of skill in the art, and are each hereby incorporated by reference in their entirety.

What is claimed:

1. A tubular tissue graft construct, comprising a tube having a lumenal surface and an exterior surface formed with an extracellular matrix material obtained from a porcine, bovine or ovine source tissue, added human vascular endothelial cells, and at least one of added human fibroblast cells and added human muscle cells, wherein the extracellular matrix material retains at least one bioactive component from said source tissue, wherein said at least one bioactive component is a growth factor, wherein the tube includes a flat sheet of extracellular matrix material formed into a tube shape and sutured or otherwise bonded to retain the tube shape, wherein said added human vascular endothelial cells are the only added cells present on the luminal surface of the tube and wherein said at least one of added human fibroblast cells and added human muscle cells is present on the exterior surface of the tube, and wherein the tubular graft construct has been prepared in vitro and is suitable for implantation in a human patient.

2. The tissue graft construct of claim 1, wherein the at least one of added human fibroblast cells and added human muscle cells includes added muscle cells.

3. The tissue graft construct of claim 2, wherein the human muscle cells are human smooth muscle cells.

4. The tissue graft construct of claim 1, wherein the at least one of added human fibroblast cells and added human muscle cells includes added human fibroblast cells.

5. The tissue graft construct of claim 1, wherein the at least one of added human fibroblast cells and added human muscle cells includes added human muscle cells and added human fibroblast cells.

6. The tissue graft construct of claim 1, wherein the at least one of added fibroblast cells and added muscle cells does not include fibroblast cells.

7. The tissue graft construct of claim 1, wherein the at least one bioactive component comprises basic fibroblast growth factor, transforming growth factor beta, epidermal growth factor, and platelet derived growth factor.

8. The tissue graft construct of claim 1, wherein said at least one growth factor comprises one or more of basic fibroblast growth factor, transforming growth factor beta, epidermal growth factor, and platelet derived growth factor.

9. The tissue graft construct of claim 8, wherein said at least one growth factor comprises basic fibroblast growth factor.

10. The tissue graft construct of claim 1, wherein said at least one bioactive component also includes heparin, heparin sulfate, hyaluronic acid, or fibronectin.

11. The tissue graft construct of claim 1, wherein the extracellular matrix material comprises submucosa tissue.

12. The tissue graft construct of claim 11, wherein the submucosa tissue is selected from the group consisting of intestinal submucosa tissue, urinary bladder submucosa tissue, stomach submucosa tissue, and uterine submucosa tissue.

13. The tissue graft construct of claim 12, wherein the submucosa tissue is intestinal submucosa tissue.

14. The tissue graft construct of claim 13, wherein the submucosa tissue is porcine.

15. The tissue graft construct of claim 1, also comprising a tubular support structure supporting the tube.

16. The tissue graft construct of claim 15, wherein the tubular support structure comprises a stent.

17. The tissue graft construct of claim 15, wherein the tubular support structure is biodegradable.

18. A method for tissue grafting, comprising vascular grafting of a human patient with a tissue graft construct of claim 1.

19. A tubular tissue graft construct, comprising:
  a tube having a lumenal surface and an exterior surface formed with an extracellular matrix material obtained from a porcine, bovine or ovine source tissue, wherein the extracellular matrix material comprises intestinal submucosa tissue that retains at least one bioactive component from said source tissue, wherein the at least one bioactive component is a growth factor, and wherein the tube includes a flat sheet of extracellular matrix material formed into a tube shape and sutured or otherwise bonded to retain the tube shape;
  added human cells on the lumenal surface of the tube, wherein the added cells on the lumenal surface of the tube consist of: (i) added human vascular endothelial cells; or, (ii) added human vascular endothelial cells and added human muscle cells;
  added human cells on the exterior surface of the tube, wherein the added human cells on the exterior surface of the tube consist of: (i) added human fibroblast cells; or, (ii) added human muscle cells; or, (iii) added human fibroblast cells and added human muscle cells; or (iv) added human fibroblast cells, added human muscle cells, and added human vascular endothelial cells; and
  wherein the tubular graft construct has been prepared in vitro and is suitable for implantation in a human patient.

* * * * *